(12) United States Patent
Jacobs et al.

(10) Patent No.: US 10,932,918 B2
(45) Date of Patent: Mar. 2, 2021

(54) POST-OPERATIVE BONE GROWTH STIMULANT INTRODUCTION METHOD

(71) Applicant: DePuy Synthes Products, Inc., Raynham, MA (US)

(72) Inventors: Scott Jacobs, Randolph, MA (US); Jeffrey Walker, Providence, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 43 days.

(21) Appl. No.: 16/163,523

(22) Filed: Oct. 17, 2018

(65) Prior Publication Data

US 2019/0046321 A1    Feb. 14, 2019

Related U.S. Application Data

(63) Continuation of application No. 15/622,396, filed on Jun. 14, 2017, now abandoned, which is a continuation of application No. 14/481,827, filed on Sep. 9, 2014, now abandoned.

(60) Provisional application No. 61/947,642, filed on Mar. 4, 2014.

(51) Int. Cl.
| | |
|---|---|
| *A61F 2/44* | (2006.01) |
| *A61F 2/30* | (2006.01) |
| *A61F 2/28* | (2006.01) |
| *A61B 90/00* | (2016.01) |

(52) U.S. Cl.
CPC ........ *A61F 2/4465* (2013.01); *A61F 2/30965* (2013.01); *A61F 2/442* (2013.01); *A61B 2090/3966* (2016.02); *A61F 2002/2817* (2013.01); *A61F 2002/2835* (2013.01); *A61F 2002/3068* (2013.01); *A61F 2002/3069* (2013.01); *A61F 2002/30593* (2013.01); *A61F 2002/30677* (2013.01); *A61F 2002/30784* (2013.01); *A61F 2002/30785* (2013.01); *A61F 2002/30787* (2013.01); *A61F 2002/30789* (2013.01); *A61F 2002/30843* (2013.01); *A61F 2310/00023* (2013.01); *A61F 2310/00359* (2013.01)

(58) Field of Classification Search
CPC ...... A61F 2/4455; A61F 2/447; A61F 2/4611; A61F 2002/2835; A61F 2002/2817; A61B 2090/3966
See application file for complete search history.

(56) References Cited

U.S. PATENT DOCUMENTS

| | | | | |
|---|---|---|---|---|
| 5,405,402 | A | * 4/1995 | Dye | A61B 90/39 623/22.38 |
| 6,049,026 | A | 4/2000 | Muschler | |
| 6,159,211 | A | * 12/2000 | Boriani | A61F 2/4455 606/279 |
| 6,287,293 | B1 | * 9/2001 | Jones | A61M 39/0208 604/502 |

(Continued)

OTHER PUBLICATIONS

Pederson, "Thermal Assembly of a Biomimetic Mineral/Collagen Composite", *Biomaterials* 24: 4881-4890 (2003).

*Primary Examiner* — Ellen C Hammond

(57) ABSTRACT

A method of revising a patient having a fusion cage implanted within a spinal column, involving percutaneously delivering a first end of a tube to the spinal column, fluidly connecting the first end of the tube to the fusion cage, and delivering a bone growth agent into the fusion cage through the tube.

18 Claims, 6 Drawing Sheets

(56) References Cited

U.S. PATENT DOCUMENTS

| | | | |
|---|---|---|---|
| 6,719,794 B2 * | 4/2004 | Gerber | A61B 17/1671 623/17.11 |
| 6,974,480 B2 * | 12/2005 | Messerli | A61F 2/4611 623/17.16 |
| 7,192,447 B2 * | 3/2007 | Rhoda | A61F 2/44 623/17.11 |
| 7,824,427 B2 | 11/2010 | Perez-Cruet | |
| 7,918,891 B1 * | 4/2011 | Curran | A61F 2/30767 623/17.16 |
| 8,118,813 B2 | 2/2012 | Perez-Cruet | |
| 8,343,224 B2 | 1/2013 | Lynn | |
| 9,039,768 B2 | 5/2015 | Voellmicke | |
| 9,168,138 B2 | 10/2015 | O'Neil | |
| 9,238,319 B2 * | 1/2016 | Gfeller | B29C 45/14467 |
| 9,693,875 B2 | 7/2017 | Ball | |
| 10,182,921 B2 | 1/2019 | Georges | |
| 2005/0234336 A1 * | 10/2005 | Beckman | A61L 31/18 600/431 |
| 2006/0089656 A1 * | 4/2006 | Allard | A61F 2/4611 606/99 |
| 2006/0104968 A1 * | 5/2006 | Bookbinder | A61K 47/60 424/94.61 |
| 2007/0041906 A1 * | 2/2007 | Lidgren | A61K 49/0409 424/9.4 |
| 2007/0093900 A1 * | 4/2007 | Williams | A61F 2/4425 623/17.11 |
| 2007/0100212 A1 * | 5/2007 | Pimenta | A61B 17/848 600/210 |
| 2011/0112639 A1 * | 5/2011 | Regala | A61B 17/56 623/13.12 |
| 2011/0166656 A1 * | 7/2011 | Thalgott | A61F 2/4465 623/17.16 |
| 2015/0216539 A1 * | 8/2015 | Reimers | A61B 17/1635 604/22 |

* cited by examiner

POST-OPERATIVE BONE GROWTH STIMULANT INTRODUCTION METHOD

CONTINUING DATA

This patent application claims priority from co-pending U.S. Ser. No. 15/622,396, filed Jun. 14, 2017, entitled "Post-Operative Bone Growth Stimulant Introduction Method", Jacobs et al., from U.S. Ser. No. 14/481,827, filed Sep. 9, 2014, entitled "Post-Operative Bone Growth Stimulant Introduction Method", Jacobs et al., and from U.S. provisional patent application U.S. Ser. No. 61/947,642, filed Mar. 4, 2014, entitled "Post-Operative Bone Growth Stimulant Introduction Method", Jacobs et al., the specifications of which are incorporated by reference in their entireties.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1β and TNF-α as well as matrix metalloproteinases ("MMPs"). These cytokines and MMPs help regulate the metabolism of the nucleus pulposus cells.

In some instances of disc degeneration disease (DDD), gradual degeneration of the intervertebral disc is caused by mechanical instabilities in other portions of the spine. In these instances, increased loads and pressures on the nucleus pulposus cause the cells within the disc (or invading macrophases) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices". The goal of a fusion device is to stabilize the motion segment associated with the problematic disc space so that a fusion can occur between the adjacent vertebrae. The conventional fusion device is typically a hollow cage that contains graft material that assists in the formation of new bone. The fusion device provides a bloody pathway between the endplates of the adjacent vertebrae for new bone to form.

Some fusion devices provide for stabilization of the functional spinal unit (FSU) in three phases. In the initial phase, the device is fixed to the FSU, typically via screws that pass through the fusion device and into the neighboring bone. In the second phase, bone grows into the device. In the third phase, bone grows through the device.

Although spinal fusion has met with significant success, there are times when the surgeon may decide to revise a patient due to symptomatic or asymptomatic non-union or fractured fusion. For example, although the anticipated fusion of the disc space generally occurs, there are times when the fusion is incomplete. For example, it has been reported that in one series 16% of the cases had intercalary pseudoarthrosis, which is visible bone ingrowth with a visible void between the bones. (Yue, ISASS, 2012). The current treatments for these situations include waiting additional time for the fusion to become complete, providing additional posterior fixation, or revising the fusion device. In such cases, a revision surgery is typically required in which the patient is re-opened and the cage removed. These revisions are expensive and pose significant safety risks to the patient.

Therefore, there is a need in cases of incomplete fusion for a suitable revision alternative to cage removal.

US 2011-0137418 (O'Neil) discloses a fusion cage having a suction tube attached thereto at a port. See FIGS. 3B and 10C.

US 2008-0154377 (Voellmicke) discloses the insertion of a fusion cage into the disc space, followed by filling the empty cage with flowable bone graft by introducing the bone graft through an annulus in the cage.

The HEALOS FX™ surgical technique discloses injecting a bone growth agent from a syringe through a cannula to an implantation site in a disc space. See FIG. 14.

SUMMARY OF THE INVENTION

The present invention relates to a novel method of revision that delivers a bone growth agent to the implanted cage. Preferably, a tube is percutaneously delivered to the cage site and docked to the cage, any tissue that has grown into the cage is removed through the tube, and bone growth agent is then delivered through the tube to the cage. This method eliminates the need for cage removal, thereby reducing the risk and cost associated with the revision.

Therefore, in accordance with the present invention, there is provided a method of revising a patient having a fusion device having a cavity implanted within a spinal column, comprising the steps of:
 a) making an incision in the patient,
 b) delivering through the incision a distal end of a tube to the spinal column, c) fluidly connecting the distal end of the tube to the cavity of the fusion device, and
d) delivering a bone growth agent into the cavity of the fusion device through the tube.

Also in accordance with the present invention, there is provided a method of revising a patient having a fusion device implanted within a disc space, comprising the steps of:
  a) making an incision in the patient,
  b) percutaneously delivering through the incision a first end of a tube to the disc space,
  c) fluidly connecting the first end of the tube to the fusion device,
  d) passing an instrument down the tube, and
  e) manipulating the instrument to alter a component of the fusion cage.

Also in accordance with the present invention, there is provided an assembly comprising:
  a) an intervertebral fusion device having a cavity and a port;
  b) a tube having a proximal end and a distal end;
  c) a bone growth transfer apparatus containing a bone growth agent;
wherein the proximal end of the tube is fluidly connected to the bone growth transfer apparatus; and
wherein the distal end of the tube is fluidly connected to the port of the fusion device.

Also in accordance with the present invention, there is provided. an intervertebral fusion cage having an anterior wall and a posterior wall connected by a pair of side walls, and a vertical throughhole, the cage further comprising a pair of radiopaque rings respectively embedded in two of the different walls, wherein the rings align.

Also in accordance with the present invention, there is provided an intervertebral fusion cage having an anterior wall and a posterior wall connected by a pair of side walls, a vertical throughhole, a docking port, and a radiopaque marker indicating the docking port.

Also in accordance with the present invention, there is provided an intervertebral fusion cage having an anterior wall and a posterior wall connected by a pair of side walls, a vertical throughhole, a docking port, and a radiopaque marker indicating the docking port.

Also in accordance with the present invention, there is provided an assembly comprising:
  a) an intervertebral fusion device having a cavity and a port;
  b) a tube having a proximal end and a distal end;
  c) a disc-manipulating instrument received in the tube,
wherein the distal end of the tube is fluidly connected to the port of the fusion device,
wherein the disc-manipulating instrument has a distal working end located in the cavity of the fusion device.

Also in accordance with the present invention, there is provided an assembly comprising:
  a) an intervertebral fusion device having a cavity and a port, wherein the port is fluidly connected to the cavity;
  b) a tube having a proximal end and a distal end;
  c) a preformed solid bone growth agent located in the tube;
wherein the distal end of the tube is fluidly connected to the port of the fusion device.

Also in accordance with the present invention, there is provided an assembly comprising:
  a) an intervertebral fusion device having a cavity and a port, wherein the port is fluidly connected to the cavity;
  b) a tube having a proximal end and a distal end;
  c) a solid carrier having a bone growth agent therein;
wherein the distal end of the tube is fluidly connected to the port of the fusion device, and
wherein the solid carrier is located in the tube.

Also in accordance with the present invention, there is provided an assembly comprising:
  a) an intervertebral fusion device having a cavity and a port, wherein the port is fluidly connected to the cavity;
  b) a solid carrier having a bone growth agent therein;
wherein the solid carrier is located in the cavity of the fusion device.

Also in accordance with the present invention, there is provided a method of revising a patient having a fusion device having a cavity implanted adjacent a bone, comprising the steps of:
  a) making an incision in the patient,
  b) delivering through the incision a distal end of a tube to the bone,
  c) fluidly connecting the distal end of the tube to the cavity of the fusion device, and
  d) delivering a bone growth agent into the cavity of the fusion device through the tube.

DETAILED DESCRIPTION OF THE INVENTION

Figure 1A:
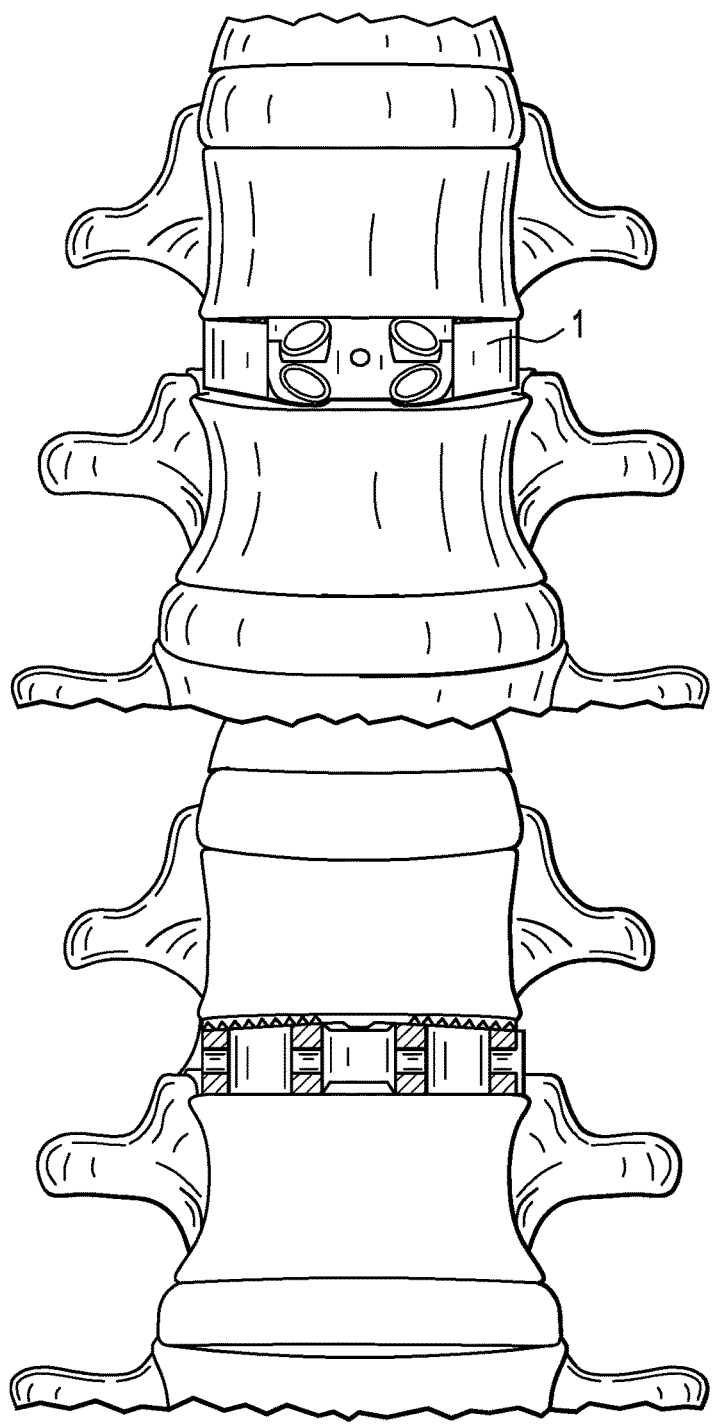
FIG. 1A discloses a conventional cage implanted in a disc space.

In some preferred embodiments, there is provided a method of revising a patient having a fusion device having a cavity implanted within a disc space, comprising the steps of:
  a) making an incision in the patient,
  b) delivering through the incision a distal end of a tube to the disc space,
  c) fluidly connecting the distal end of the tube to the cavity of the fusion device, and
  d) delivering a bone growth agent into the cavity of the fusion device through the tube.

In some embodiments, a pusher is used to push the bone growth agent through a tube into the cavity.

In some preferred embodiments, the method of revising a patient having a fusion cage having a cavity, wherein the cage is implanted within a disc space, comprises the steps of:
  a) making an incision in the patient,
  b) percutaneously delivering through the incision a distal end of a tube to the disc space,
  c) fluidly connecting the distal end of the tube to the fusion cage,
  d) using lavage to remove non-bony tissue from the cavity of the fusion cage,
  e) fluidly connecting the proximal end of the tube to a bone growth agent transfer apparatus; and f) delivering a bone growth agent from the bone growth agent transfer apparatus into the cavity of the fusion cage through the tube.

Before surgically undertaking revision of the cage, it is necessary to first locate the cage in the patient. If the revision procedure is to be carried out percutaneously (so that a direct line-of-sight to the cage is unavailable), then the surgeon must first radiographically locate the fusion cage within the patient. This can be accomplished by using radiology to align a pair of radiopaque rings located in the fusion cage. When the rings are aligned, the surgeon knows the orientation of the cage relative to the perspective of the imaging device.

Next, preferably, the tube is delivered to the fusion cage in a percutaneous manner, thereby minimizing the invasiveness of the procedure. In other embodiments, however, the tube may be delivered through an open procedure.

The tube can have a radiographic marker (such as a ring) placed at its distal end in order to track the tube radiographically as it travels from the patient's skin to the fusion cage. This radiographic tracking of the tube guarantees that the tube will always move towards the cage. Once the distal end of the tube reaches the cage, it can dock onto a port provided on the cage. This port provides a fluid connection between the tube and the internal cavity of the cage. Likewise, the port of the cage can be surrounded by a radiographic marker ring, so that the surgeon can easily direct the distal end of the tube towards the port to which it will dock.

Before delivering the bone growth agent to the cage, it is useful to remove any non-bony tissue that has grown into the cage from the surrounding vertebrae because it is the intent of the revision of the present invention to replace this non-bony tissue with bony tissue. In these cases, the percutaneous tube can be used as an access port through which a combination fluid jet-aspirator is delivered to the disc space. The fluid jet creates a lavage of the site and cuts non-bony tissue within the cage, while the aspirator removes the cut tissue from the cage. Typically, the fluid used for the lavage is saline. In some embodiments, the tissue removed from the device is non-bony tissue. In others, the tissue removed from the device includes both non-bony and bony tissue.

Once the tissue is cleared, the combination fluid jet-aspirator is removed from the tube and the proximal end of the tube is fluidly connected to a bone growth transfer apparatus. In some embodiments, this apparatus may be a simple syringe loaded with bone paste. Typically, the connection of the bone growth transfer apparatus and the proximal end of the tube is accomplished via mating Luer-locks situated on the proximal end of the tube and the distal end of the bone growth transfer apparatus.

Next, the bone growth agent is delivered from the bone growth transfer apparatus to the cavity within the fusion cage by actuating the bone growth transfer apparatus. When a syringe is used as the bone growth transfer apparatus and so stores the bone growth agent, this may be accomplished by simply depressing the plunger on the syringe. The delivery of the bone growth agent should be carried out until the cavity within the cage is filled with bone growth agent.

In some embodiments, after the bone growth agent is delivered to the cage but before the tube is removed, a plug may be inserted into the port in order to prevent the bone growth agent from leaking out the opening of the port. Alternatively, the plug may be replaced with a self-sealing membrane. In some embodiments, the plug/membrane can be inserted with the fusion device in the original procedure. In other embodiments, the plug/membrane can be inserted into the fusion device during the revision.

Once the cage is re-filled with a bone growth agent, the tube is removed from the cage and the patient is closed.

Although delivering a flowable bone growth agent to the implanted cage is a preferred embodiment of the present invention, it is anticipated that there are other ways of revising the cage. In some embodiments, the revision may be simply altering a component of the fusion cage. This alteration may be carried out by a step selected from the group consisting of exchanging the component, manipulating the component, adjusting the component, adding a component, and removing a component of the fusion device. By way of example, in one embodiment, a pin or screw may be removed to allow motion in a previously-locked device, or to increase the motion in a constrained-motion device.

It is also contemplated by the present invention to approach, prepare, place and/or retain additional bone growth agent outside or partially inside the device. In some embodiments thereof, additional bone growth agent may also be delivered to locations outside of the fusion cage. This step would seek to stabilize the spine in areas other than the disc space of concern. In some embodiments thereof, the additional bone growth agent is delivered adjacent a facet joint of the FSU of concern. For example, there may be placement and retention of a bone marrow aspirate-soaked ChronOS™ strip to the facet area of the desired level via a percutaneous posterior approach.

In preferred embodiments, the bone growth agent is provided in a flowable form and travels through the tube by fluid convection. However, in other embodiments, the bone growth agent may travel through the tube in a solid carrier that is pushed through the tube. In some embodiments thereof, this solid carrier can snap into the fusion cage, while in others this solid carrier threads into the fusion cage. The solid carrier may be delivered to the implanted fusion cage as an empty carrier that is then filled with bone growth agent by the surgeon. Alternatively, the solid carrier may be delivered to the implanted fusion cage filled with a collagen sponge, with additional fluid bone growth agent to be added by the surgeon. The solid carrier may further be delivered to the implanted fusion cage filled with a scaffold material, with additional fluid bone growth agent to be added by the surgeon. In some embodiments, a plug/cap with a diaphragm is provided in order to facilitate injection of these fluids.

In some embodiments, the tube approaches the implanted fusion cage along the same pathway used to originally implant the fusion cage. In others, the tube approaches the implanted fusion cage from a pathway different than that used to originally implant the fusion cage. The approach taken by the tube to the implanted cage can include but is not limited to an anterior approach, a lateral approach, a far lateral approach, a posterior approach or an axial (L5-S1) approach.

Figure 1B:
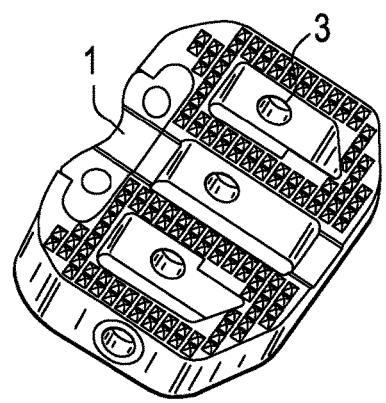
FIGS. 1B-1C disclose a fusion cage having radiopaque rings.
Figure 1C:
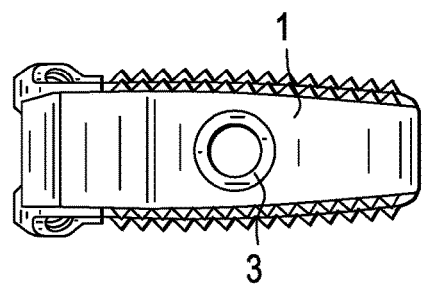
Figure 2A:
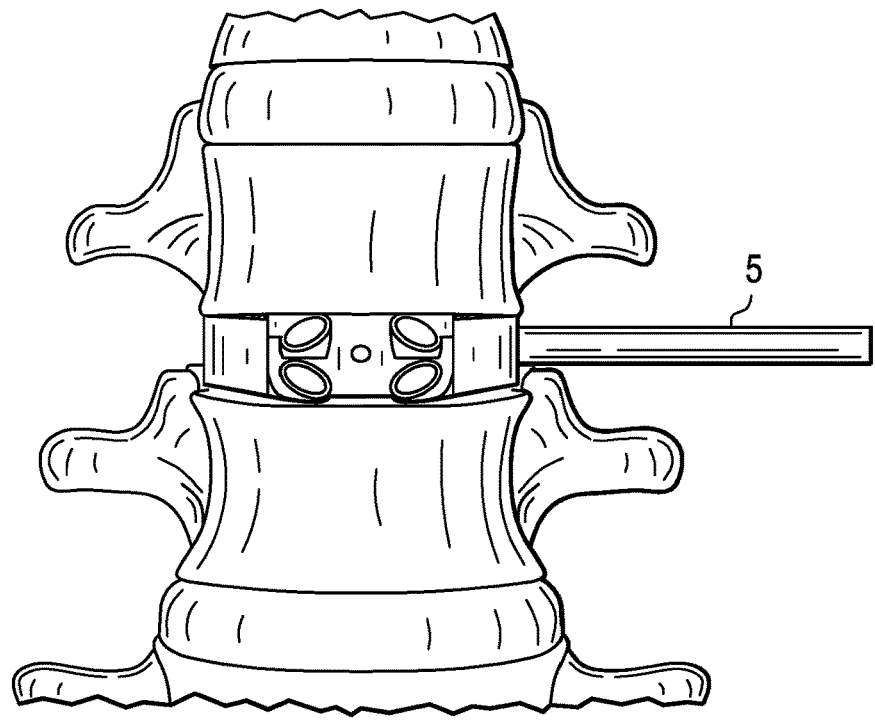
FIGS. 2A-2B disclose a tube approach and docking to an implanted fusion device.
Figure 2B:
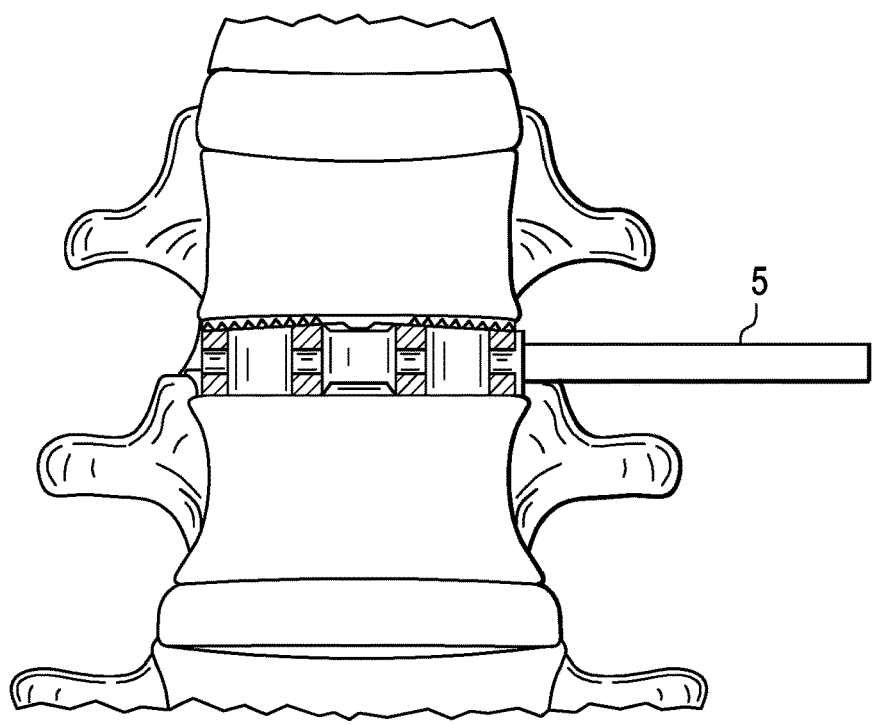
Figure 3:
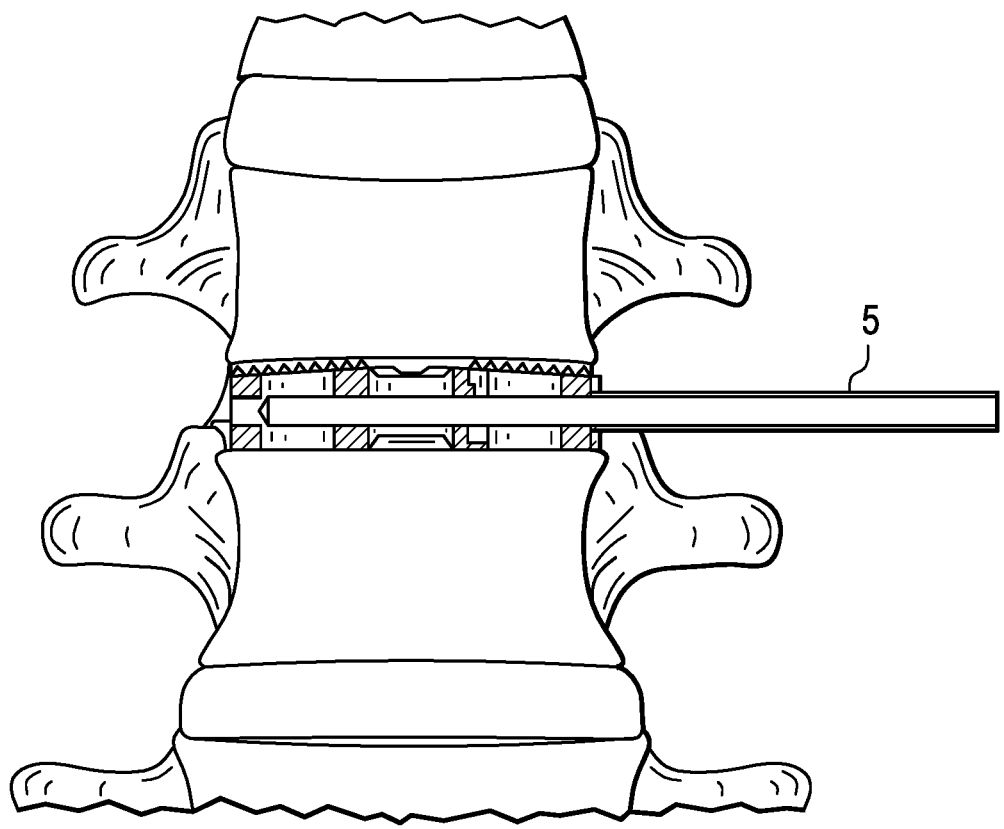
FIG. 3 discloses an implanted cage with tissue removed.
Figure 4:
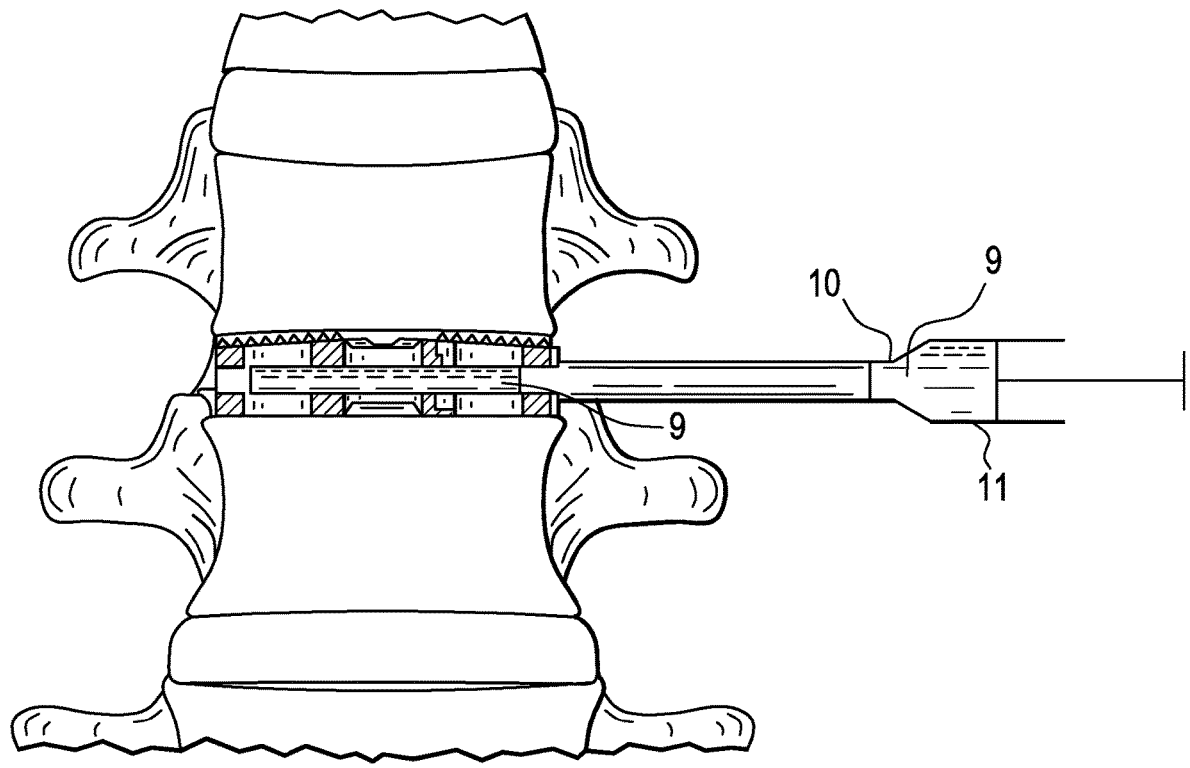
FIG. 4 discloses the delivery of the bone growth agent to the fusion device.
Figure 5:
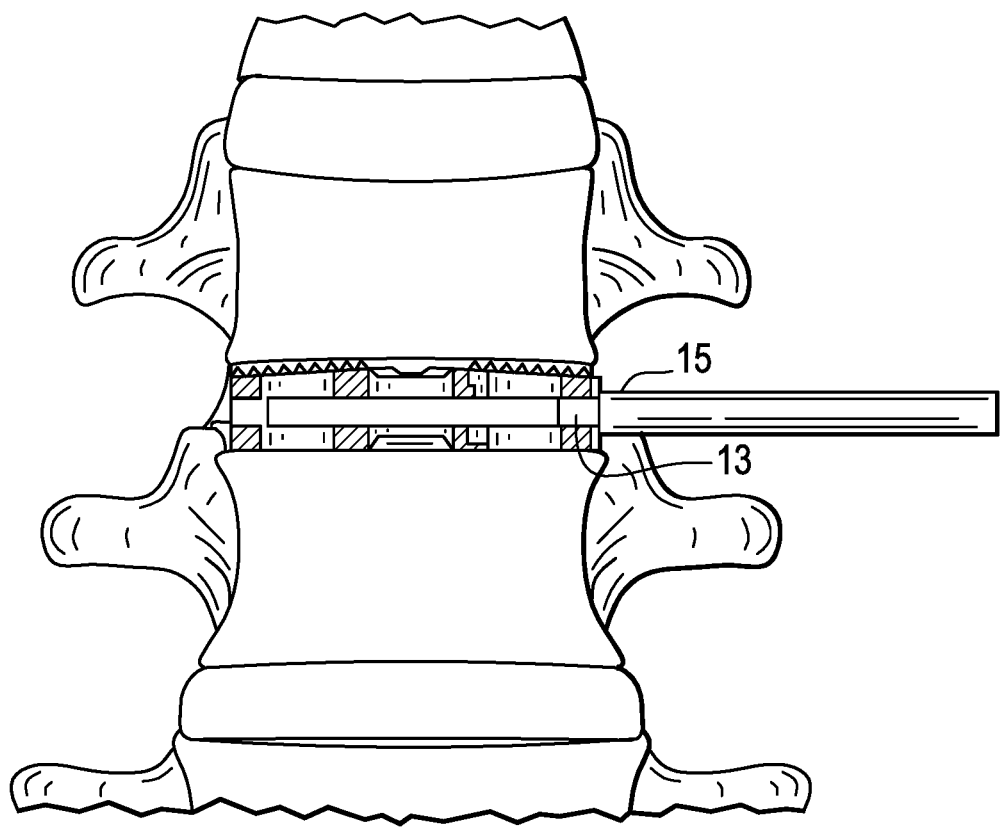
FIG. 5 discloses removal of the tube from the port on the fusion device.
Figure 6:
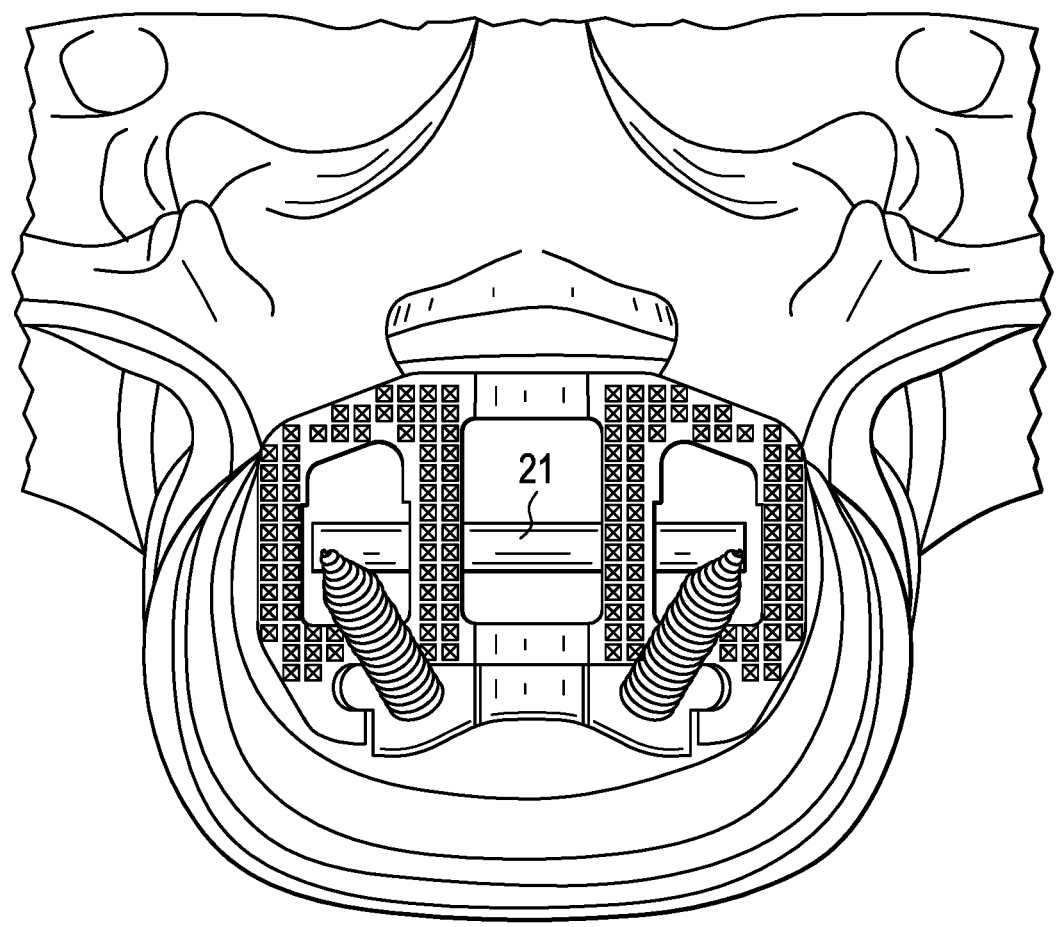
FIG. 6 discloses a revised cage of the present invention.

Now referring to FIGS. 1a-1c, the surgeon locates the fusion device 1 within the patient with radiographic imaging by aligning the radiopaque rings 3 of the device. Now referring to FIGS. 2a-2b, the tube 5 approaches the fusion device and docks to the fusion device. Now referring to FIG. 3, the physician opens a canal in the fusion device by removing non-bony tissue with the fusion device. Now referring to FIG. 4, the physician inserts bone growth agent 9 into the cavity of the fusion device by actuating syringe 11, which is attached to the proximal end 10 of the tube. Now referring to FIG. 5, the distal end 15 of the tube is then removed from the port 13 of the fusion cage. Lastly, the physician radiographically verifies placement of the revised device. FIG. 6 shows a revised cage of the present invention having a cylindrically-shaped preformed bone growth agent 21 therein.

In some embodiments of the present invention, there is provided an assembly comprising:
a) an intervertebral fusion device having a cavity and a port;
b) a tube having a proximal end and a distal end;
c) a bone growth transfer apparatus containing a bone growth agent;
wherein the proximal end of the tube is fluidly connected to the bone growth transfer apparatus; and
wherein the distal end of the tube is fluidly connected to the port of the fusion device.

In some embodiments, the bone growth agent is a non-autologous bone growth agent, while in others the bone growth agent is a synthetic bone growth agent.

In some embodiments, the port is surrounded by a radiographic ring.

In some embodiments, the tube is sized to extend from the skin of a patient to a disc space in the patient.

In accordance with the present invention, there is provided an intervertebral fusion cage having an anterior wall and a posterior wall connected by a pair of side walls, and a vertical throughhole, the cage further comprising a pair of radiopaque rings respectively embedded in two of the different walls, wherein the rings align.

In accordance with the present invention, there is provided an intervertebral fusion cage having an anterior wall and a posterior wall connected by a pair of side walls, a vertical throughhole, a docking port, and a radiopaque marker indicating the docking port.

Preferably, the radiopaque marker is a ring that surrounds the docking port, and the docking port is in fluid communication with the vertical throughhole.

In accordance with the present invention, there is provided an intervertebral fusion cage having an anterior wall and a posterior wall connected by a pair of side walls, a vertical throughhole, and a plurality of docking ports adapted to receive a tube.

Preferably, each docking port is in fluid communication with the vertical throughhole, and at least one of the docking ports is located in a sidewall.

In some embodiments, the cage has a distal end of a tube received in one of the docking ports, and has a bone growth transfer apparatus containing a bone growth agent fluidly connected to a proximal end of the tube.

In accordance with the present invention, there is provided an assembly comprising:
a) an intervertebral fusion device having a cavity and a port;
b) a tube having a proximal end and a distal end;
c) a disc-manipulating instrument received in the tube, wherein the distal end of the tube is fluidly connected to the port of the fusion device,
wherein the disc-manipulating instrument has a distal working end located in the cavity of the fusion device.

In some embodiments, the disc-manipulating instrument is adapted to remove non-bony tissue from the cavity of the fusion device, or is adapted to cut a vertebral endplate.

Preferably, the disc-manipulating instrument is either a drill, a rasp, or a loop cutter.

In some embodiments, the tube, drill and pusher are assembled outside the patient. For example, the tube, drill and pusher are assembled at the manufacturing facility. In other embodiments, the tube, drill and pusher are inserted piece-by-piece in the patient.

In accordance with the present invention, there is provided an assembly comprising:
a) an intervertebral fusion device having a cavity and a port, wherein the port is fluidly connected to the cavity;
b) a tube having a proximal end and a distal end;
c) a preformed solid bone growth agent located in the tube;
wherein the distal end of the tube is fluidly connected to the port of the fusion device.

Preferably, the preformed solid bone growth agent has a cylindrical shape, and has a length substantially equal to a length of the cavity of the fusion device.

In accordance with the present invention, there is provided an assembly comprising:
a) an intervertebral fusion device having a cavity and a port, wherein the port is fluidly connected to the cavity;
b) a tube having a proximal end and a distal end;
c) a solid carrier having a bone growth agent therein;
wherein the distal end of the tube is fluidly connected to the port of the fusion device, and
wherein the solid carrier is located in the tube.

In some embodiments, the solid carrier snaps into or threads into the fusion cage.

In accordance with the present invention, there is provided an assembly comprising:
a) an intervertebral fusion device having a cavity and a port, wherein the port is fluidly connected to the cavity;
b) a solid carrier having a bone growth agent therein;
wherein the solid carrier is located in the cavity of the fusion device.

Preferably, the solid carrier snaps into the fusion cage, or threads into the fusion cage.

The method of the present invention supports the principles of sound spinal surgery management. It supports anatomic reduction because the anatomic relationships remain unchanged from the initial procedure. It supports stable fixation by docking directly to a dedicated feature (port) on the implant, so that previously placed hardware is not disturbed. It supports preservation of the blood supply, as creation of the canal (via tissue removal) for the bone growth agent removes non-bony tissue and may cause bleeding only in the area of the desired bone growth. Lastly, it supports early mobilization, as the small incision and minimal tissue reduction allow patients to return home on the same day as the revision with only minor post-operative discomfort.

Complimentary technologies may also be used to assist the revision surgery of the present invention. In some embodiments, image guided surgery equipment and instruments may be used to plan the incision, guide the tube to the implanted fusion device, and guide instruments through tissue dissection. Intraoperative neuromonitoring may be used to guide the approach of the tube to the fusion device, particularly when taking a lateral approach. In some embodiments, the probe and dilator from ORACLE™, available from DePuy Synthes Spine of Raynham, Mass., USA. may be used. In some embodiments, the SPOTLIGHT™ retractor available from DePuy Synthes Spine of Raynham, Mass., USA. may be used.

It is anticipated that the method of the present invention can be carried out upon a conventional intervertebral fusion cage. These include PLIF cages, TLIF cages, ALIF cages and lateral cages.

The intervertebral fusion cage of the present invention may be manufactured from any biocompatible flexible material suitable for use in interbody fusion procedures. In some embodiments, the cage comprises a composite comprising 40-99% polyarylethyl ketone PAEK, and optionally 1-60% carbon fiber. Such a cage is radiolucent. Preferably, the polyarylethyl ketone PAEK is selected from the group consisting of polyetherether ketone PEEK, polyether ketone ketone PEKK, polyether ketone ether ketone ketone PEKEKK, and polyether ketone PEK. Preferably, cage is made from woven, long carbon fiber laminates. Preferably, the PAEK and carbon fiber are homogeneously mixed. In some embodiments, the composite consists essentially of PAEK and carbon fiber. In some embodiments, the composite comprises 60-80 wt % PAEK and 20-40 wt % carbon fiber, more preferably 65-75 wt % PAEK and 25-35 wt % carbon fiber. In some embodiments, the cage is made from materials used in carbon fibers cages marketed by DePuy Synthes Spine, Raynham, Mass., USA. In some embodiments, the composite is PEEK-OPTIMA™, available from Invibio of Greenville, N.C.

In other embodiments, the cage is made from a flexible metal such as a titanium alloy such as nitinol.

In other embodiments, the cage is made from structural allograft or xenograft.

In preferred embodiments, the cage is provided in a sterile form.

In some embodiments, the bone growth agent may be HEALOS FX™, a flowable collagen-based material available from DePuy Synthes Spine of Raynham, Mass., USA. In other embodiments, the bone growth agent may be ChronOS™, a tricalcium phosphate material available from DePuy Synthes Spine of Raynham, Mass., USA. In other embodiments, the bone growth agent may be a CONFORM™ cube or cylinder, a demineralized bone material available from DePuy Synthes Spine of Raynham, Mass., USA. In other embodiments, the bone growth agent may be DBX™, a demineralized bone matrix material available from DePuy Synthes Spine of Raynham, Mass., USA.

In some embodiments, a PMMA bone cement is injected into the fusion device. In preferred embodiments, this PMMA bone cement is the CONFIDENCE™ bone cement, available from DePuy Synthes Spine of Raynham, Mass., USA, and it is injected with the CONFIDENCE™ cement injection system, available from DePuy Synthes Spine of Raynham, Mass., USA, In some embodiments, the bone forming agent is a growth factor. As used herein, the term "growth factor" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-β superfamily, including TGF-β1, 2 and 3; osteoid-inducing factor (OIF), angiogenin(s); endothelins; hepatocyte growth factor and keratinocyte growth factor; members of the bone morphogenetic proteins (BMPs) BMP-1, BMP-3, BMP-2, OP-1, BMP-2A, BMP-2B, BMP-7 and BMP-14, including HBGF-1 and HBGF-2; growth differentiation factors (GDFs), members of the hedgehog family of proteins, including indian, sonic and desert hedgehog, ADMP-1; bone-forming members of the interleukin (IL) family; rhGDF-5; and members of the colony-stimulating factor (CSF) family, including CSF-1, G-CSF, and GM-CSF, and isoforms thereof.

In some embodiments, these growth factors can be supplied through an implantable pump that is docked to the cage during the primary or revision surgery.

In some embodiments, platelet concentrate is provided as the bone forming agent. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the bone, and because its fibrin matrix provides a suitable scaffold for new tissue growth.

In some embodiments, the bone forming agent comprises an effective amount of a bone morphogenic protein (BMP). BMPs beneficially increasing bone formation by promoting the differentiation of mesenchymal stem cells (MSCs) into osteoblasts and their proliferation.

In some embodiments, between about 1 ng and about 10 mg of BMP are administered into the target disc space. In some embodiments, between about 1 microgram (μg) and about 1 mg of BMP are administered into the target disc space.

In many preferred embodiments, the bone forming agent is a porous matrix, and is preferably injectable.

The porous matrix of the present invention may contain porous or semi-porous collagen, extracellular matrices, metals (such as Ti, Ti64, CoCr, and stainless steel), polymers (such as PEEK, polyethylene, polypropylene, and PET) resorbable polymers (such as PLA, PDA, PEO, PEG, PVA, and capralactides), bone substitutes (such as TCP, HA, and CaP), autograft, allograft (such as allograft beads), xenograft, and/or blends thereof. Matrices may be orientated to enable flow from bony attachment locations to the aspiration port. Matrices may be layered with varying densities, pore structures, materials to enable increase stem filter at desired locations via density, pore size, affinity, as well as fluid flow control (laminar, turbilant, and/or tortuous path).

In some embodiments, the porous matrix is a mineral. In one embodiment, this mineral comprises calcium and phosphorus. In some embodiments, the mineral is selected from the group consisting of calcium phosphate, tricalcium phosphate and hydroxyapatite. In one embodiment, the average porosity of the matrix is between about 20 and about 500 μm, for example, between about 50 and about 250 μm. In yet other embodiments of the present invention, in situ porosity is produced in the injected matrix to produce a porous scaffold in the interbody space. Once the in situ porosity is produced in the space, the surgeon can inject other therapeutic compounds into the porosity, thereby treating the surrounding tissues and enhancing the remodeling process of the target tissue.

In some embodiments, the mineral is administered in a granule form. It is believed that the administration of granular minerals promotes the formation of the bone growth around the minerals such that osteointegration occurs.

In some embodiments, the mineral is administered in a settable-paste form. In this condition, the paste sets up in vivo, and thereby immediately imparts post-treatment mechanical support to the interbody space.

In another embodiment, the treatment is delivered via injectable absorbable or non-absorbable cement to the target space. The treatment is formulated using bioabsorbable macro-sphere technologies, such that it will allow the release of the bone forming agent. The cement will provide the initial stability required to treat pain in target tissues. These tissues include, but are not limited to, hips, knee, vertebral body and iliac crest. In some embodiments, the cement is selected from the group consisting of calcium phosphate, tricalcium phosphate and hydroxyapatite. In other embodiments, the cement is any hard biocompatible cement, including PMMA, processed autogenous and allograft bone. Hydroxylapatite is a preferred cement because of its strength and biological profile. Tricalcium phosphate may also be used alone or in combination with hydroxylapatite, particularly if some degree of resorption is desired in the cement.

In some embodiments, the porous matrix comprises a resorbable polymeric material.

In some embodiments, the bone forming agent comprises an injectable precursor fluid that produces the in situ formation of a mineralized collagen composite. In some embodiments, the injectable precursor fluid comprises:
 a) a first formulation comprising an acid-soluble type I collagen solution (preferably between about 1 mg/ml and about 7 mg/ml collagen) and
 b) a second formulation comprising liposomes containing calcium and phosphate.

Combining the acid-soluble collagen solution with the calcium- and phosphate-loaded liposomes results in a liposome/collagen precursor fluid, which, when heated from room temperature to 37° C., forms a mineralized collagen gel.

In some embodiments, the liposomes are loaded with dipalmitoylphosphatidylcholine (90 mol %) and dimyristoyl phosphatidylcholine (10 mol %). These liposomes are stable at room temperature but form calcium phosphate mineral when heated above 35° C., a consequence of the release of entrapped salts at the lipid chain melting transition. One such technology is disclosed in Pederson, *Biomaterials* 24: 4881-4890 (2003), the specification of which is incorporated herein by reference in its entirety.

Alternatively, the in situ mineralization of collagen could be achieved by an increase in temperature achieved by other types of reactions including, but not limited to, chemical, enzymatic, magnetic, electric, photo- or nuclear. Suitable sources thereof include light, chemical reaction, enzymatically controlled reaction and an electric wire embedded in the material. To further elucidate the electric wire approach, a wire can first be embedded in the space, heated to create the calcium deposition, and then withdrawn. In some embodiments, this wire may be a shape memory such as nitinol that can form the shape. Alternatively, an electrically-conducting polymer can be selected as the temperature raising element. This polymer is heated to form the collagen, and is then subject to disintegration and resorption in situ, thereby providing space adjacent the mineralized collagen for the bone to form.

In some embodiments, the osteoconductive material comprises calcium and phosphorus. In some embodiments, the osteoconductive material comprises hydroxyapatite. In some embodiments, the osteoconductive material comprises collagen. In some embodiments, the osteoconductive material is in a particulate form.

Specific matrices may be incorporated into the device to provide load bearing qualities, enable directional bone formation, and/or control density of regenerated bone (cortical vs cancellous) or enable cell formation for soft tissue attachment. Nanotubes or nanocrystals can be orientated in a generally axial direction to provide for load bearing abilities as well as capillary wicking of vascular flow to further enhance directional bone formation. Biocompatible nanotubes can currently be produced from either carbon or titanium or bone substitutes including Ca, HA, and TCP.

In one embodiment, the bone forming agent is a plurality of viable ex vivo osteoprogenitor cells. Such viable cells, introduced into the interbody space, have the capability of at least partially supplementing the in situ drawn stem cells in the generation of new bone for the interbody space.

In some embodiments, these cells are obtained from another human individual (allograft), while in other embodiments, the cells are obtained from the same individual (autograft). In some embodiments, the cells are taken from bone tissue, while in others, the cells are taken from a non-bone tissue (and may, for example, be mesenchymal stem cells, chondrocytes or fibroblasts). In others, autograft osteocytes (such as from the knee, hip, shoulder, finger or ear) may be used.

In one embodiment, when viable ex vivo cells are selected as an additional therapeutic agent or substance, the viable cells comprise mesenchymal stem cells (MSCs). MSCs provide a special advantage for administration into the interbody space because it is believed that they can more readily survive the relatively harsh environment present in the space, that they have a desirable level of plasticity; and that they have the ability to proliferate and differentiate into the desired cells.

In some embodiments, the mesenchymal stem cells are obtained from bone marrow, such as autologous bone marrow. In others, the mesenchymal stem cells are obtained from adipose tissue, preferably autologous adipose tissue.

In some embodiments, the mesenchymal stem cells injected into the interbody space are provided in an unconcentrated form, e.g., from fresh bone marrow. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated herein by reference in its entirety, can be used. In some embodiments, the matrix used to filter and concentrate the MSCs is also administered into the interbody space.

In some embodiments, bone cells (which may be from either an allogeneic or an autologous source) or mesenchymal stem cells, may be genetically modified to produce an osteoinductive bone anabolic agent which could be chosen from the list of growth factors named herein. The production of these osteopromotive agents may lead to bone growth.

Recent work has shown that plasmid DNA will not elicit an inflammatory response as does the use of viral vectors. Genes encoding bone (anabolic) agents such as BMP may be efficacious if injected into the uncoupled resorbing bone. In addition, overexpression of any of the growth factors provided herein or other agents which would limit local osteoclast activity would have positive effects on bone growth. In one embodiment, the plasmid contains the genetic code for human TGF-β or erythropoietin (EPO).

Accordingly, in some embodiments, the additional therapeutic agent is selected from the group consisting of viable cells and plasmid DNA.

A matrix may be made from hydrogels or may incorporate a hydrogel as component of the final structure. A hydrogel may be used to expand and enhance filling, improve handling characteristics or increase vacuum pressure. The increased vacuum pressure may be used to determine adequate hydration/stem cell filtration.

In some cases, excess bone marrow aspirate can be collected and mixed with added graft extenders including collagen like the HEALOS™, and HEALOS FX™, each of which is available from DePuy Synthes Spine, Raynham, Mass., USA In some embodiments, the bone growth agent is a synthetic bone growth agent.

In some embodiments, the bone growth agent is a non-autologous bone growth agent.

There are a number of ways in which the instruments and devices of the present invention can be delivered from the manufacturer to the surgeon. The instruments can be provided as traditional non-sterile sets, in a sterile pack that is returned for reprocessing; and in a sterile pack that is single use. The implants can be delivered sterile or non-sterile. The complete set can be delivered sterile.

Although the present invention has been described with reference to its preferred embodiments, those skillful in the art will recognize changes that may be made in form and structure which do not depart from the spirit of the invention.

We claim:

1. A method of revising a patient having a fusion device having a cavity implanted within a spinal column, comprising the steps of:
    a) making an incision in the patient having the fusion device having the cavity implanted within the spinal column,
    b) delivering through the incision a distal end of a tube to the spinal column,
    c) fluidly connecting the distal end of the tube to the cavity of the fusion device, and
    d) delivering a bone growth agent into the cavity of the fusion device through the tube,
further comprising, between steps c) and d), the step of:
    e) removing tissue from the cavity of the fusion device.

2. The method of claim 1 wherein tissue removal is accomplished with lavage.

3. The method of claim 1 wherein, in step c), the tube connects to a port on the fusion device.

4. The method of claim 3 wherein the port is associated with a radiographic marker.

5. The method of claim 1 further comprising, before step d), the step of:
    e) fluidly connecting a bone growth transfer apparatus containing a bone growth agent to a proximal end of the tube.

6. The method of claim 1 further comprising, before step a), the step of:
    e) radiographically locating the fusion device within the patient.

7. The method of claim 6 wherein step e) includes radiographically aligning a pair of radiopaque rings located in the fusion device.

8. The method of claim 1 further comprising the step of:
    e) altering a component of the fusion device.

9. The method of claim 8 wherein the alteration is carried out by a step selected from the group consisting of exchanging the component, manipulating the component, adjusting the component, adding a component, and removing a component.

10. The method of claim 1 further comprising the step of:
    e) delivering additional bone growth agent to a location outside of the fusion device.

11. The method of claim 10 wherein the additional bone growth agent is delivered adjacent a facet joint.

12. The method of claim 1 wherein the bone growth agent travels through the tube by fluid convection.

13. The method of claim 1 wherein the bone growth agent travels through the tube in a solid carrier.

14. The method of claim 13 wherein the solid carrier snaps into the fusion device.

15. The method of claim 13 wherein the solid carrier threads into the fusion device.

16. The method of claim 13 wherein the solid carrier is filled with a collagen sponge during delivery to the fusion device.

17. The method of claim 13 wherein the carrier is filled with a scaffold material during delivery to the fusion device.

18. The method of claim 1 wherein the bone growth agent is flowable.

* * * * *